United States Patent [19]
Reigstad et al.

[11] Patent Number: 6,119,526
[45] Date of Patent: Sep. 19, 2000

[54] METHOD AND APPARATUS FOR DETECTING TENDON FAILURES WITHIN PRESTRESSED CONCRETE

[75] Inventors: Gordon H. Reigstad, White Bear Lake; Hanley S. Reigstad, Sunburg, both of Minn.

[73] Assignee: Tech Research, Inc., St. Paul, Minn.

[21] Appl. No.: 09/116,034

[22] Filed: Jul. 15, 1998

Related U.S. Application Data

[63] Continuation-in-part of application No. 08/864,776, May 29, 1997, abandoned.

[51] Int. Cl.$^7$ .................................................. G01N 3/00
[52] U.S. Cl. ............................................. 73/803; 324/218
[58] Field of Search ........................... 73/760, 762, 763, 73/768, 774, 779, 784, 786, 866.5, 803; 324/217, 218, 225, 234

[56] References Cited

U.S. PATENT DOCUMENTS

| | | |
|---|---|---|
| 4,574,545 | 3/1986 | Reigstad et al. . |
| 4,799,307 | 1/1989 | Reigstad et al. . |
| 4,814,705 | 3/1989 | Saunderson . |
| 4,928,451 | 5/1990 | Reigstad et al. . |
| 5,296,807 | 3/1994 | Kousek et al. . |
| 5,481,929 | 1/1996 | Kohlert et al. . |
| 5,540,096 | 7/1996 | Woodcock et al. . |
| 5,618,999 | 4/1997 | Schweitzer et al. . |

OTHER PUBLICATIONS

Rotary Shaft Encoder #380, Electro–Sensor, Inc., pp. 1–4, Published before the filing date of the present application.
Redar Datascan C–4974, NDT James Instruments, Inc., pp. 1–15, Published before the filing date of the present application.

*Primary Examiner*—Max Noori
*Attorney, Agent, or Firm*—Merchant & Gould P.C.

[57] ABSTRACT

A nondestructive detection apparatus for detecting tendon failures in a prestressed concrete slab. The detection apparatus includes a cart adapted to be moved over the prestressed concrete slab. A metal sensor and a distance meter are connected to the cart. As the cart is moved over the slab, the metal sensor takes readings of a length of tendon and the distance meter measures the distance traversed by the cart. The detection apparatus also includes a controller that interfaces with the metal sensor and the distance meter. The controller is constructed and arranged to sample the readings generated by the metal sensor at predetermined distance intervals traversed by the cart.

26 Claims, 13 Drawing Sheets

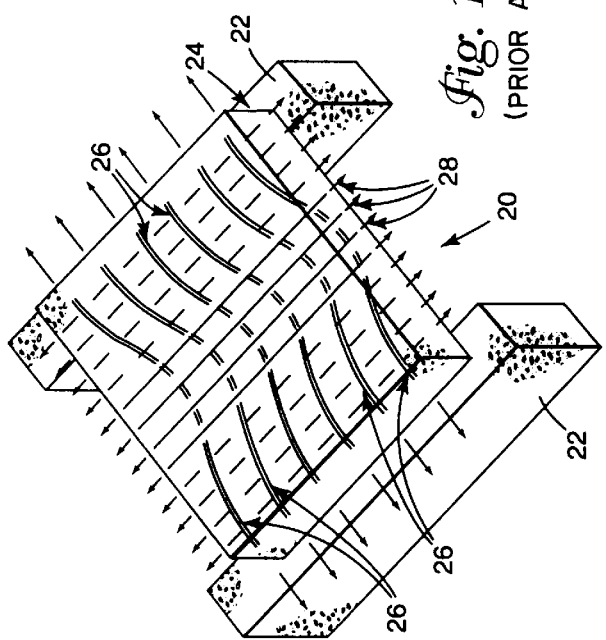
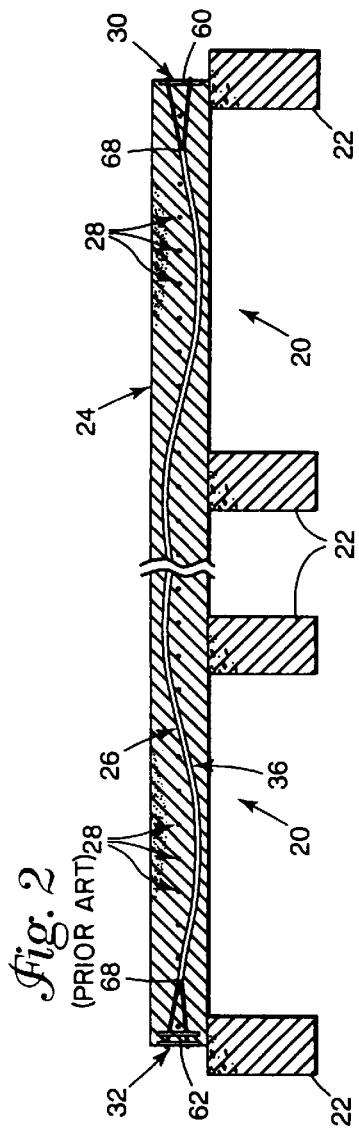

METHOD AND APPARATUS FOR DETECTING TENDON FAILURES WITHIN PRESTRESSED CONCRETE

CROSS-REFERENCE TO RELATED U.S. APPLICATIONS

The present application is a continuation-in-part of U.S. patent application Ser. No. 08/864,776, filed on May 29, 1997, which is currently abandoned.

FIELD OF THE INVENTION

The present invention relates generally to methods and apparatuses for detecting failures in reinforcing steel within concrete structures. More particularly, the present invention relates to methods and apparatuses for nondestructively identifying tendon failures in prestressed concrete slabs.

BACKGROUND OF THE INVENTION

Prestressed concrete is a type of reinforced concrete that has been subjected to an external compressive force prior to the application of loads. The compressive force is typically provided by steel tendons within the concrete that are initially tensioned with hydraulic jacks and held in tension by end anchors.

Prestressed concrete is categorized as either pre-tension or post-tension. Pre-tension refers to the method of first stressing tendons and then casting concrete around the prestressed tendons. The concrete cures before releasing the prestressed tendons and transferring the stress from the tendons to the concrete. Post-tension refers to the method of casting concrete around unstressed tendons and then stressing the tendons after the concrete has reached a specified strength.

Although the modern method of prestressing concrete may be traced to the late 1920's, its general use in the United States did not begin until the late 1940's or early 1950's. General acceptance and the primary increase in use occurred primarily between 1965 and 1975. Application of prestressing was being made in all aspects of construction including buildings, towers, floating terminals, ocean structures and ships, storage tanks, nuclear containment vessels, bridge piers, bridge decks, foundations, soil anchors, and virtually all other types of installations where normal reinforced concrete was acceptable. Thus, prestressed concrete and methods for its initial installation for diverse applications is now well known.

After years of service, however, problems associated with prestressed concrete structures became apparent. The problems primarily related to the premature deterioration of prestressed concrete structures and the subsequent task of identifying and repairing the deteriorated structures before they experienced complete loss of structural integrity.

It is now known that the chloride ion is responsible for the premature deterioration/corrosion of reinforcement steel within concrete. The chloride ion, typically in the form of calcium chloride or sodium chloride, is commonly used on roadways and bridges as a de-icer. Automobiles carry chloride ions to concrete structures such as parking ramps (ie. garages). Once in contact with a concrete structure, the chloride ions leach or otherwise move into the concrete and react with the reinforcement steel within the concrete causing corrosion/deterioration. Due to the corrosive effects of the chloride ion, bridges and parking structures estimated to have useful maintenance free lives of 10 to 25 years are now requiring maintenance in only 7 to 15 years.

The corrosion of prestressed steel is a serious problem that can compromise the structural integrity of a bridge or parking structure with minimal visual signs. Consequently, the early detection of steel failure within a structure is a major safety issue for parking structure and bridge owners. Without detection, steel corrosion can occur to the point of collapse without any major outward visual signs.

Methods of locating steel failures can be categorized as either destructive or nondestructive. Destructive methods involve the removal, often via a jack hammer, of concrete to allow the steel to be physically/visually inspected. Consequently, destructive test methods require some degree of repair after the testing has been completed. By contrast, nondestructive test methods do not require repair after the testing has been completed.

There are many nondestructive tests that are applied to concrete and provide information as to the structural integrity of the concrete. To a limited degree, information provided by such tests can be used to make a semi-educated evaluation regarding the structural integrity of the steel within the concrete. However, to date there is no economical nondestructive method of examining long lengths of prestressing steel with the intent of locating failures. For the most part, existing nondestructive test methods have been limited to the examination of small areas of concrete slab for the sole purpose of locating pretension steel. Examining the entire length of a steel reinforcement with the intent of discovering failures has not been attempted on a systematic large scale production oriented basis.

What is needed is a efficient and reliable nondestructive test method for evaluating the structural integrity of an entire structure such as a bridge or parking ramp. What is also needed is a nondestructive test method for charting entire lengths of reinforcing steel within a structure to identify steel failures. Also what is needed is a method for providing a graphical representation of all of the prestressing steel within a given structure.

SUMMARY OF THE INVENTION

The present invention relates to a nondestructive detection apparatus for detecting tendon failures within a reinforced concrete slab. The detection apparatus includes a cart adapted to be moved over the concrete slab along a length of tendon. A metal detector and a distance meter are connected to the cart. As the cart is moved over the concrete slab, the metal detector takes readings representative of the steel tendon and the distance meter measures the distance traversed by the cart. The detection apparatus also includes a controller that interfaces with the metal detector and the distance meter. The controller is constructed and arranged to sample the readings generated by the metal detector at predetermined distance intervals along the tendon.

The present invention also relates to a method for nondestructively detecting tendon failures in a reinforced concrete slab. The method includes the step of first locating a length of tendon within the concrete slab. Next, a metal detector is moved along the length of tendon so as to take a consecutive series of readings along the tendon. The readings are sampled at predetermined locations along the length of the tendon. The sampled readings are plotted versus the corresponding locations along the length of the tendon so as to generate a profile for the length of the tendon. The profile provides a visual representation of the tendon that can be used to quickly and easily identify tendon failure locations.

The present invention further relates to a nondestructive detection apparatus for detecting tendon failures that includes an auto-centering mechanism for automatically centering a sensing probe over a tendon being sensed. In certain embodiments, the centering mechanism includes a scanning lead sensor that is laterally oscillated across the tendon as the detection apparatus is moved longitudinally along the tendon.

The importance of the present invention can be appreciated when one considers that depending on the type of steel tendons employed, a building slab such as a one way garage slab will have 100 to 200 linear feet of steel tendon for each parking space. Thus, a 1500 car garage may have 30 to 60 miles of steel tendon, all of which is required to be sound. A two way post tensioned slab would have approximately twice as many deck/slab tendons.

The present invention provides an apparatus and method for quickly and reliably evaluating, on a large scale basis, the degree of tendon deterioration within a given structure. By practicing the present invention, tendon failures can be identified without having to physically inspect the tendons or destroy the overlaying slab. Unlike spot checking, the present invention can be used to provide tendon profiles for all of the steel in a given structure. Each deck can be systematically mapped out so as to clearly illustrate specific failure areas that are in need of repair. Such information is extremely valuable for maintaining a structure and for estimating repair costs.

A variety of additional advantages of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. A brief description of the drawings is as follows:

FIG. 1 is a perspective view of a portion of a prestressed slab as it extends between two beams;

FIG. 2 is a cross-sectional, side-elevation illustration showing a typical profile of a primary stressing tendon;

DETAILED DESCRIPTION OF THE PREFERRED EMBODIMENT

Figure 3:
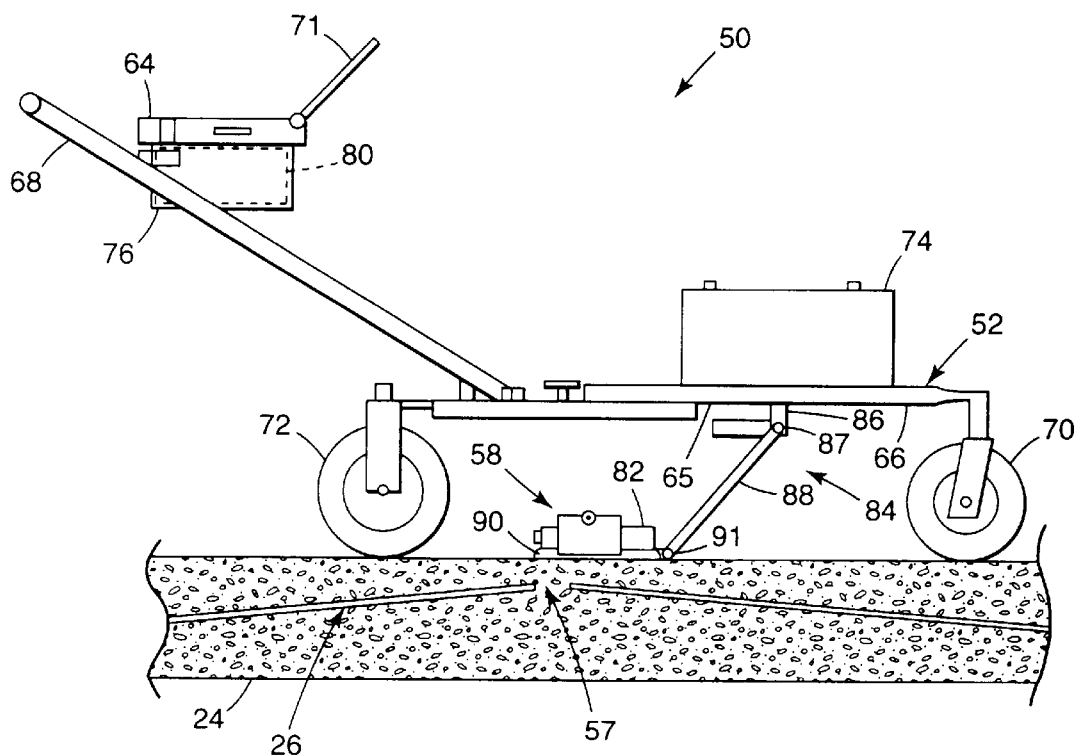
FIG. 3 is a side view of a nondestructive detection apparatus constructed in accordance with the principles of the present invention.

Reference will now be made in detail to exemplary embodiments of the present invention which are illustrated in the accompanying drawings. Wherever possible, the same reference numbers will be used throughout the drawings to refer to the same or like parts.

FIG. 1 shows a typical bay 20 that includes a pair of spaced-apart parallel beams 22 that support a slab 24. The slab 24 is prestressed with primary tendons 26 extending in one direction and temperature tendons 28 extending in a direction traverse to the primary tendons 26.

When a concrete slab is supported by separate beams, the dead load of the concrete slab along with any live loads applied to the top of the slab cause the slab to bow downward at mid span between the support beams. When the slab bows downward, the top half of the slab at mid span is placed in compression while the bottom half of the slab at mid span is placed in tension. At the support beams, the top of the slab is placed in tension while the bottom of the beam is subject to compression. Concrete has high compressive strengths and relatively low tension strengths. Consequently, the tension present in the slab can lead to cracking and premature failure of the slab.

Post tensioning is a technique that optimizes the high compressive strength characteristics of concrete by using tensioned steel to minimize tension within a concrete slab. FIG. 2 shows a typical profile for a tensioning tendon 26. The tendon 26 is essentially formed in a wave pattern having high portions over beams and low portions midway between beams. A dead anchor 30 and a stressing anchor 32 are attached at opposite ends. When a tensile force is applied at the stressing anchor, the lower portions of the tendon 26 raise the slab 24 slightly while the higher portions of the tendons 26 compress downwardly onto the beams 22. The stressed tendon 26 slightly bows the slab 24 upwardly between the beams 22 thereby reducing the tension on the lower portion of the slab 24. Desirably, sufficient tensile force is applied to the slab 24 to place the entire thickness of the slab 24 into compression.

By using post tensioning steel, concrete slabs can be made thinner than is possible through the use of non-tensioned reinforcing steel. However, because the thin slabs depend greatly upon the tensioning steel for strength, it is important for tendon deterioration or failure to be detected at an early stage.

Figure 4:
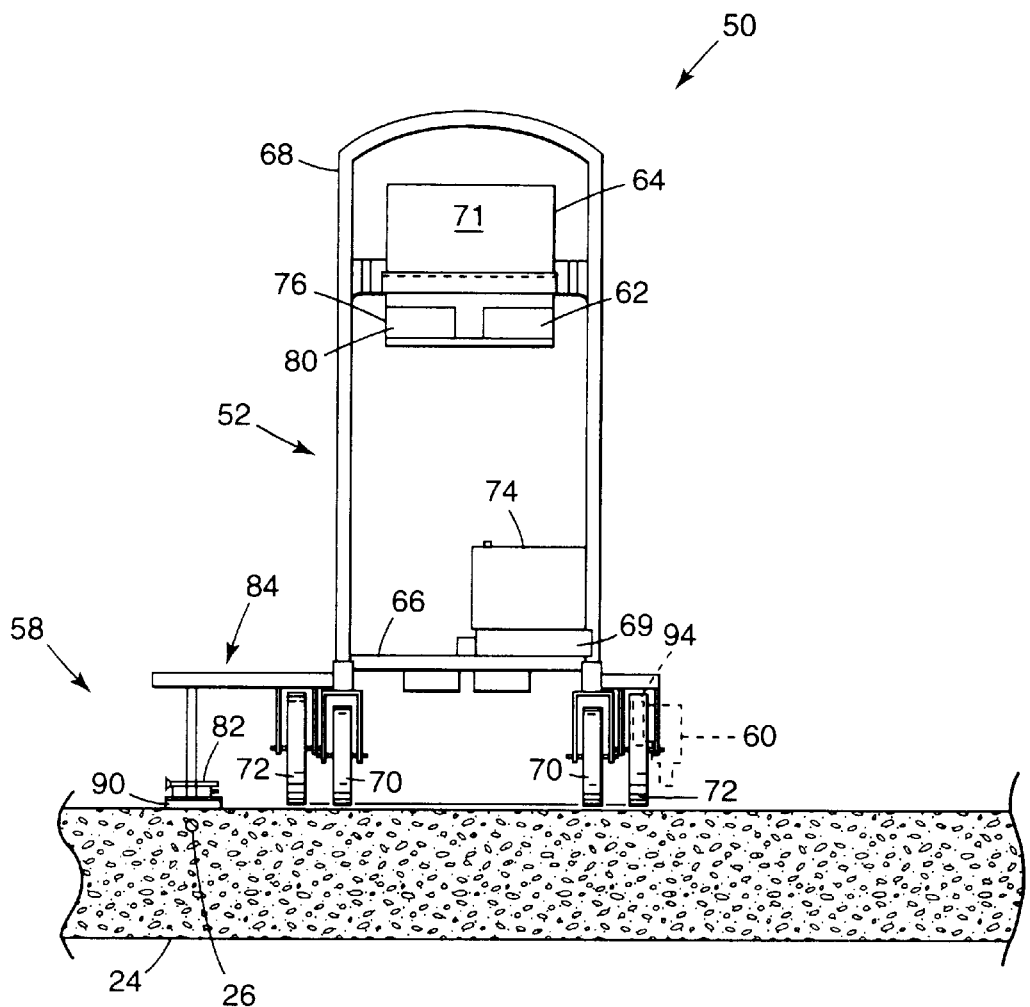
FIG. 4 is a front view of the apparatus of FIG. 3.
Figure 5:
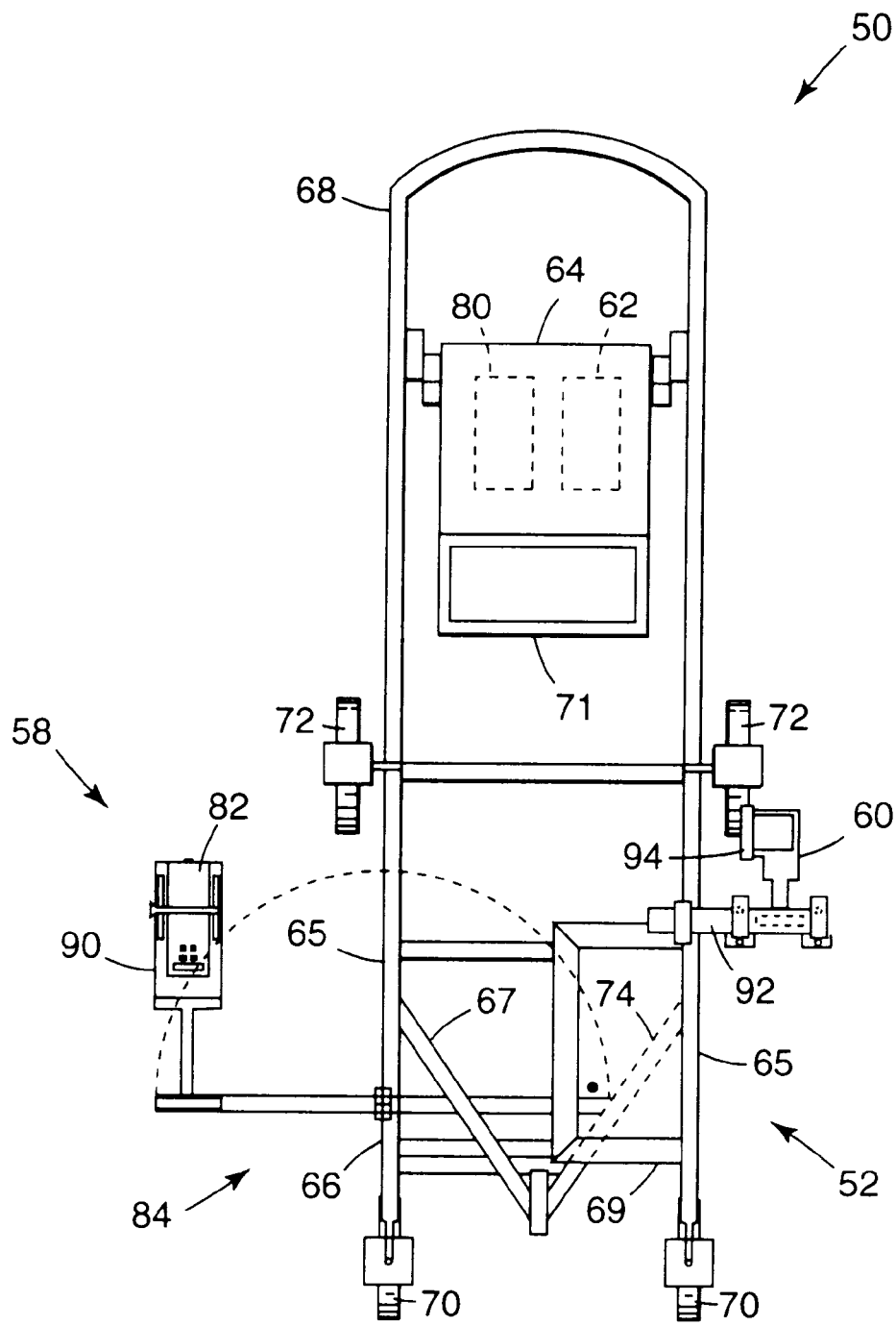
FIG. 5 is a top view of the apparatus of FIG. 3.
Figure 7:
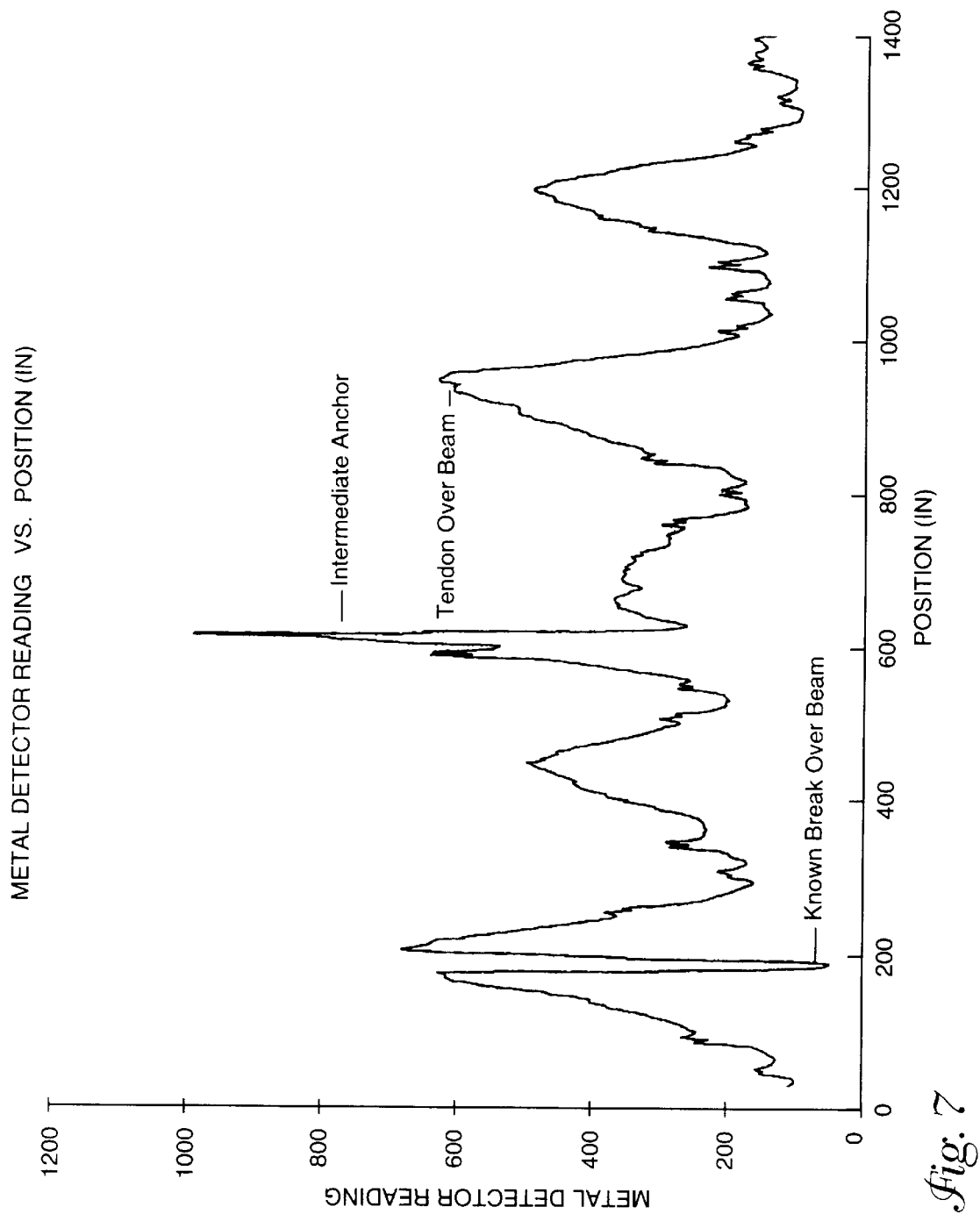
FIG. 7 is a graph illustrating an exemplary profile for a length of tendon.

FIGS. 3–5 illustrate a nondestructive detection apparatus 50 constructed in accordance with the principles of the present invention. The detection apparatus 50 includes a cart 52 adapted to be moved over the top of a prestressed concrete slab 24 along a length of tensioned tendon 26. A ferrous material detector 58 and a distance meter 60 are connected to the cart 52. As the cart 52 is moved over the concrete slab 24, the ferrous material detector 58 takes readings of the tendon 26 that are used to identify tendon failures 57, and the distance meter 60 measures the distance traversed by the cart 52. A micro-controller 62 interfaces with both the ferrous material detector 58 and the distance meter 60. At predetermined distance intervals traversed by the cart 52, the micro-controller 62 samples the readings generated by the ferrous material detector 58 and converts the readings from analog signals to digital signals. The digital signals are sent from the micro-controller 62 to a processing unit such as a personal computer 64. As shown in FIGS. 3–5, the computer 64 comprises a lap top computer having a display screen 71 pivotally connected to the main unit. The personal computer 64 processes the digital signals, calculates corresponding distance data, and generates a graph in which the data generated by the detector 58 is plotted versus the corresponding distance data to produce a profile (as shown in FIG. 7) for the length of tendon 26.

The cart 52 is preferably constructed of a semi-rigid material such as metal, fiberglass or plastic and preferably includes a base 66 having a handle 68 connected thereto. The base 66 includes side members 65 that are interconnected by a generally triangular shaped interior support frame 67. A rectangular tray or platform 69 is mounted on the support frame 67 and functions to hold or retain a power source 74 such as a deep cell battery. A pair of casters 70 are connected to the front of the base 66 while a pair of non-swiveling wheels 72 are connected to the back of the base 66. As best shown in FIGS. 4 and 5, the non-swiveling wheels 72 are outwardly offset from the sides 65 of the base 66. When the cart 52 is pushed by the handle 68, the casters 70 facilitate steering the cart 52.

The cart 52 also includes an open ended box 76 connected to the handle 68. The top of the box 76 forms a platform for supporting the computer 64. The interior of the box 76 is sized to contain portions of the ferrous material detector 58 and the micro-controller 62.

The ferrous material detector 58 is preferably a sensitive metal detector. Typically, the ferrous material detector 58 produces a field and measures or reads variations in this field caused by the presence of a ferrous material such as steel. The ferrous material detector 58 generates readings or signals that are representative of the amount of ferrous material present in the concrete and the distance the ferrous material is located from the ferrous material detector 58.

As shown in FIGS. 3–5, the ferrous material detector 58 includes a control unit 80 that is electronically coupled to a sensor or probe 82. The control unit 80 is preferably housed within the box 76 on the handle 68 of the cart 52. The probe 82 is preferably connected to the base 66 of the cart 52 by a pivot linkage 84.

The pivot linkage 84 includes a generally horizontal first link 86 that is pivotally connected to the base 66 of the cart 52. The first link 86 can be pivoted along a generally horizontal plane from an outwardly extending position and a stowed position. The pivot linkage 84 also includes a second link 88 that is pivotal connected to the first link 86. One end of the second link 88 is free to pivot about a first axis 87 that is longitudinally aligned with the first link 86. The other end of the second link 88 is pivotal connected to the front end of a slide plate 90 upon which or the probe 82 is mounted. The slide plate 90 is free to pivot about a second axis 91 that is substantially parallel to the first axis 87.

The dual pivot structure of the second link 88 allows the slide plate 90 to maintain a sliding contact with the top surface of the concrete slab 24. The slide plate 90 places the probe 82 in close proximity to the top of the concrete slab such that accurate and reliable readings of the tendon 26 can be obtained. Additionally, the slide plate 90 and the second link 88 are preferably constructed of a non-magnetic material such as plastic so as to not interfere with the operation of the ferrous material detector 58. It will be appreciated that the detection apparatus 50 can also be configured to take readings along a bottom surface of a slab.

It will be appreciated that the ferrous material detector 58 can be connected to the cart 52 in a variety of ways and in a variety of locations. For example, in alternative configurations, the sensor 82 could be aligned with a central longitudinal axis of the cart 52 rather than offset from the side 65 of the cart 62.

An exemplary ferrous material detector is a metal detector manufactured and distributed by James Instruments Inc. under the name "Rebar Datascan C-4974". Such a device can also be used to detail other metals such as aluminum. Although the magnetic field generating properties of ferrous materials makes metal detectors or other types of conventionally known metal detectors/sensors ideally suited for use in association with the present invention, it will be appreciated that alternative sensors may also be used. For example, sensors utilizing X-rays can also be used to generate an image of structural steel within a slab. Additionally, a half-cell sensing device using the principle of a half-cell battery can be employed to give an indication as to the present state of corrosion in prestressing steel within a concrete slab. Half-cell readings are relative, thus, the prestressing steel must be monitored at time intervals to comparatively map the progress of corrosion along a given steel tendon. It will be appreciated that half-cell reading can not be used to directly locate failed prestressing steel. However, half-cell readings can be used to identify tendon locations having levels of corrosion indicative of tendon failure.

The distance meter 60 of the detection apparatus 50 is preferably an odometer or other type of device for measuring the distance traveled by the cart 52. As shown in FIG. 5, the distance meter 60 is mounted on a transverse member 92 connected to one of the side members 65 of the cart base 66. The distance meter 60 includes a wheel 94 mounted on a rotary shaft (not shown). The outer radial surface of the wheel 94 engages the outer radial surface of one of the wheels 72 of the cart 52. The movement of the cart 52 causes the wheel 72 to rotate which in turn causes the wheel 94 and rotary shaft of the distance meter 60 to rotate. The distance meter 60 converts the rotation of the rotary shaft into pulses or signals which are representative of the linear distance traversed by the cart 52. For example, a preferred pulse rate is 30 pulses per linear inch traversed by the cart 52. However, it will be appreciated that the pulse rates can be varied without departing from the principles of the present invention. It will further be appreciated that the pulses also provide rate, position, and direction of rotation information.

An exemplary distance meter is available under the name "Rotary Shaft Encoder #380" from "Electro-Sensors, Inc." of Minnetonka, Minn.

The micro-controller 62 of the detection apparatus 50 is housed in the box 76 of the cart 52. The micro-controller 62 preferably includes A/D circuitry for converting analog signals received from the ferrous material detector 58 into digital signals that can be processed by the personal computer 64. The micro-controller 62 preferably also includes circuitry for counting the pulses generated by the distance meter 60 and for sampling the readings generated by the ferrous material detector 58 at a predetermined pulse interval. For example, if the distance meter 60 generates 30 pulses per linear inch traversed by the cart 52, it would be desirable for the micro-controller 62 to sample the readings generated by the ferrous material detector/sensor 58 every 30 pulses.

Although it is preferred to take one magnetic reading sample per linear inch traversed by the cart 52, this rate is merely exemplary and is not intended to be construed as a limitation upon the invention. For example, if more precision is required, the magnetic readings can be sampled at a higher frequency than once per inch. Alternatively, if less precision is required, the magnetic reading can be sampled at a lower frequency than once per inch.

FIGS. 3–5 also provide wiring diagrams showing how the component parts of the detection apparatus 50 are electrically interconnected. The wiring configuration of the detection apparatus 50 is described in a wiring table as follows:

Wiring Table

| Wire Code | # of Wires | From | To |
|---|---|---|---|
| I | 1 | Probe/Sensor | Detector Control Unit |
| II | 2 | Power Source | Micro-controller |
| III | 1 | Distance meter | Micro-controller |
| IV | 2 | Detector Control Unit | Micro-controller |
| V | 1 | Micro-controller | Laptop Computer |

Figure 6:
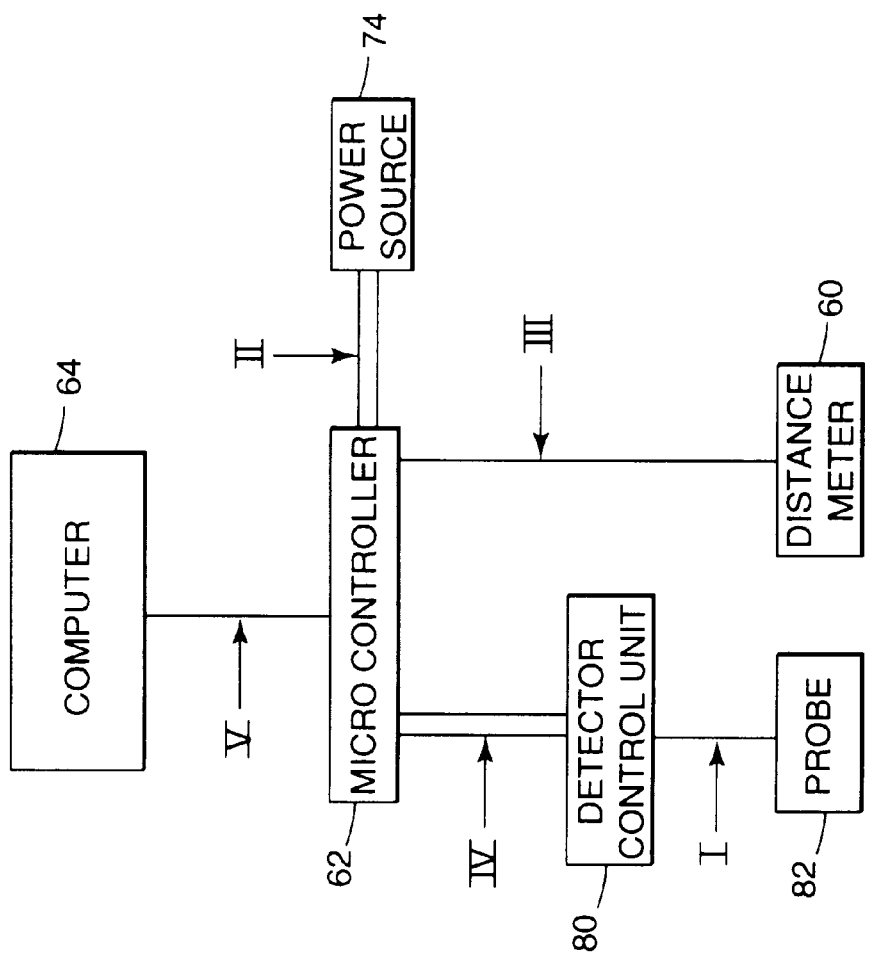
FIG. 6 is a schematic diagram illustrating a wiring configuration for the apparatus of FIGS. 3–5.

As illustrated in FIG. 6 and described in the above wiring table, the probe/sensor 82 of the ferrous material detector 58 is connected to the control unit 80 by a wire I. The power source 74 is connected to the micro-controller 62 by dual wires II. The distance meter 60 is connected to the micro-controller 62 by a single wire III. The control unit 80 is connected to the micro-controller 62 by dual wires IV. Finally, the micro-controller 62 is connected to the lap top computer 64 by a wire V such as a serial port.

As previously described, the detection apparatus 50 is used to nondestructively identify corrosion or failures in tendons within a reinforced concrete slab. An exemplary use for the detection apparatus 50 is to test the primary tendons 26 within the prestressed concrete slab 24 of the parking structure bay 20 of FIG. 1. Essentially, the detection apparatus 50 is used to map out tendon Profiles for each of the tendons 26.

The first step in the detection/mapping process is typically to identify and locate the primary tendons 26 within the bay 20. The tendons 26 are located by moving the detection apparatus 50 preferably perpendicularly across the tendons 26. As the detection apparatus 50 is moved across a specific tendon 26, the detection apparatus 50 detects the presence of the tendon 26 and alerts an operator of the detection apparatus 50. The operator then marks the tendon 26 by placing a paint or chalk mark on the concrete slab 24 directly above the tendon 26. The detection apparatus 50 is moved transversely across the primary tendons 26 until at least two separate points have been identified on each tendon 26. Once two separate points on a particular tendon have been identified, the operator can string line between the two identified points to identify the location of the entire length of tendon.

Once a length of tendon has been identified and marked, the operator is ready to map out a tendon profile of the identified length of tendon. To test the length of tendon, the first link 86 of the pivot linkage 84 is moved to the operating position such that the slide plate 90 and the probe 82 are offset from the side 65 of the cart 52. Next, the operator powers up the detection apparatus 50 and pushes the cart 52 such that the slide plate 90 slides over the concrete slab directly above the identified length of tendon. As the cart 52 moves along the marked length of tendon, the ferrous material detector/sensor 58 continuously takes readings, such as reluctance readings, of the portion of tendon 26 that is located directly below the probe 82 and the distance meter 60 measures the distance traversed by the cart 52. Every time the cart 52 traverses a predetermined distance interval, the micro-controller 62 samples the reading/signal generated by the ferrous material detector/sensor 58.

Upon receipt of a sampled reading, the micro-controller 62 converts the reading from an analog signal to a digital signal and then sends the converted digital signal to the personal computer 64. The personal computer 64 receives the digital signal from the micro-controller 62, calculates corresponding distance data, and generates a graph in which the digital readings are plotted versus the corresponding distance data to produce a profile for the length of tendon. For each reading sampled by the micro-controller 62, the processing unit 64 generates a pair of representative x and y coordinate values. For example, the x-coordinate might be representative of the relative magnitude of a reading taken by the ferrous material detector 58 and the y-coordinate might be representative of the exact location over the tendon at which the reading was taken.

FIG. 7 is a graph showing a representative tendon profile/map that has been generated using the above-described testing technique. On the graph, a first parameter representative of the relative magnitudes of exemplary readings generated by the ferrous material detector 58 is plotted verses a second parameter representative of distances (in) traversed by the cart 52. Each plotted point on the graph has an x-coordinate and a corresponding y-coordinate. The x-coordinate is representative of a particular location along the length of tendon, and the corresponding y-coordinate is representative of a reading taken by the detector 58 at the particular location along the tendon. For example, the zero position is representative of the initial starting point of the cart 52 at the beginning of a length of tendon. At the zero position, a representative reading of approximately 175 is shown on the graph. The subsequent positions are representative of the linear distance traversed along the length of tendon from the initial starting point of the cart 52. For example, the 600 position is representative of a position on the tendon located 600 inches from the initial starting point of the cart 52.

It will be appreciated that the value of the y-coordinate need not be equal to the actual reading. Instead, the y-coordinate values, as shown in FIG. 7, are representative and dependent upon the actual readings generated by the detector 58. Consequently, the actual magnitudes of the y-coordinate values are not significant. Instead, information regarding the positioning of the tendon within the slab can be drawn from the relative magnitudes of the y-coordinate values.

The tendon profile of FIG. 7 shows a series of peaks and valleys. The peaks represent locations where the tendon is close to the top surface of the concrete slab such that a high reading is generated. Peaks typically represent locations over the support beams. The valleys represent locations where the tendon is located far away from the probe such that a low reading is generated. Valleys typically represent the midpoints between support beams. Inconsistencies or gaps in the profile waves are typically representative of failure points in the tendon. For example, in the graph of FIG. 6, a tendon failure is indicated at approximately 190 inches from the initial starting point of the test.

It will be appreciated that a tendon profile as shown in FIG. 7 is preferably progressively displayed on the screen 71 of the computer 64 as an operator moves the cart 52 along a length of tendon. In this manner, the operator can immediately identify and mark tendon failures during the mapping/testing procedure. After traversing an entire length of tendon, the resultant profile can be saved in memory, such as memory associated with the computer or memory remote from the computer. A hard copy of the profile can also be generated by a printer linked to the computer.

With the above-described method of detection, tendon failures within a given tendon can be pinpointed without having to destroy the surrounding concrete. Furthermore, the coordinates generated by the above-described method can be stored in memory associated with the computer or associated with a home station and used to map out the tendon profiles for entire decks. By mapping out the tendon profiles for entire decks, any damaged or broken tendons can be easily identified and marked for future repair. Furthermore, with this method of detection, entire structures can be charted or mapped such that any tendon failures within the structure can be pinpointed.

An alternative method for utilizing the detection apparatus 50 relates to a grid method. In using a grid method, a specific area of concrete slab is first designated for testing. For example, a 20 foot by 20 foot section of slab may be designated. Once the area of slab is designated, the detection apparatus is moved in multiple passes across the section. For example, a series of parallel passes may be made across the section. A preferred spacing between consecutive passes is one inch.

As the apparatus 50 is moved across the section, the detector 58 generates readings representative of the underlying steel and the distance meter 60 generates distance data representative of the location of the apparatus 50 within the specified area of slab. The data generated by the distance meter 60 and metal detector 58 are preferably stored in memory associated with the computer 64 and used to plot a grid illustrating the steel configuration within the designated area of concrete slab.

Figure 8:
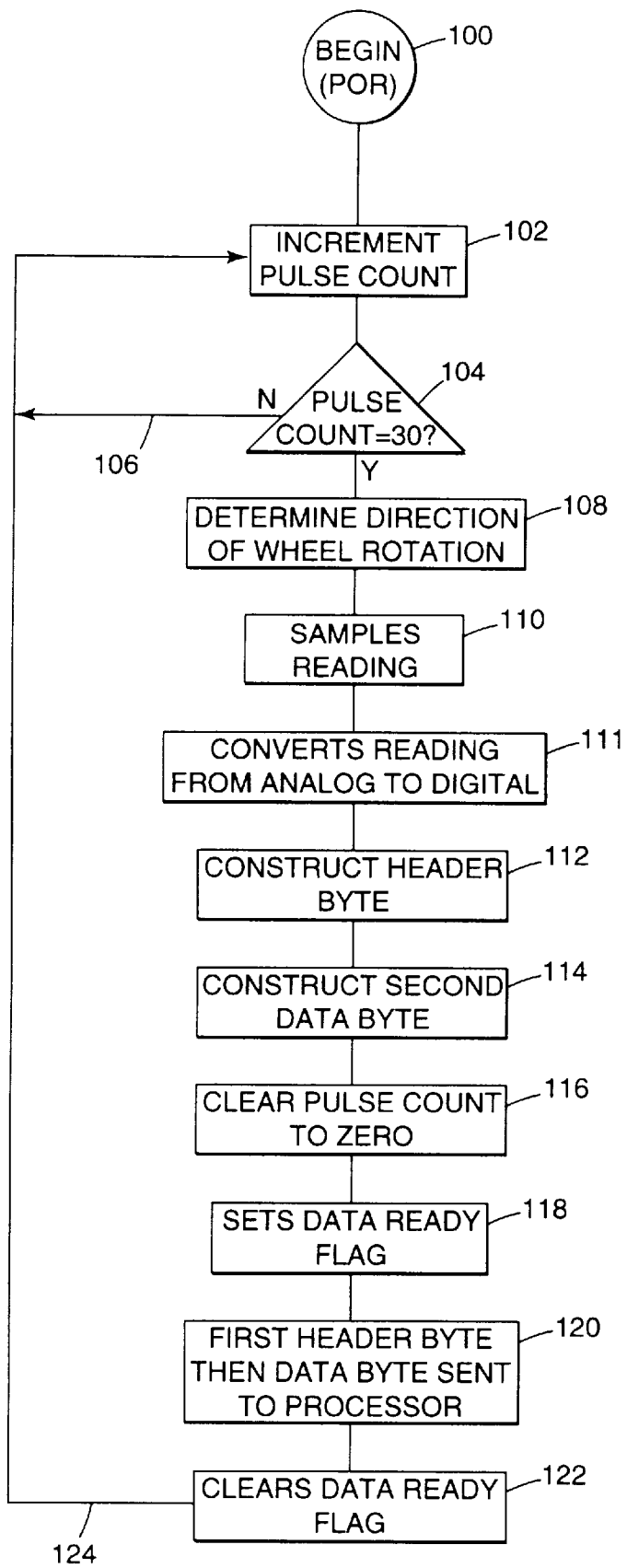
FIG. 8 is a flow chart illustrating micro-controller flow logic suitable for use with the present invention.

FIG. 8 is a software flow chart illustrating exemplary control logic suitable for use with the micro-controller 62. Specifically, the flow chart demonstrates an interrupt routine for causing the micro-controller 62 to sample the readings generated by the ferrous material detector 58 at predetermined distance intervals.

As shown in the flow chart at circle 100, the system is first powered up and variables and ports are initialized. Once the system is powered up, an operator can begin testing a tendon by moving the cart 52 along a length of the tendon 58. As the cart 52 is moved along the length of tendon, the distance meter 60 generates a certain number of pulses per inch, for example, 30 pulses per inch. At box 102, the micro-controller 62 counts the pulses and at triangle 104 checks if the pulse count equals n. If the pulse count is less than n, the sequence loops back via line 106 and the microprocessor 62 continues counting the pulses. However, when the pulse count equals n, an interrupt routine is triggered.

Once the interrupt routine is triggered, the micro-controller 62, at box 108, determines the direction in which the cart 52 is proceeding and at box 110 samples a reading from the ferrous material detector 58. At box 111, the reading is converted by the micro-controller 62 from analog to digital. Next, at box 112, the micro-controller constructs a first byte that is a header. The first byte contains a bit indicating that it is a header, a bit indicating the wheel rotation direction of the cart, and the six most significant bits of the magnetic reading generated by the detector 58.

As shown by box 114, the micro-controller 62 then constructs a second byte containing additional bits of data from the digitized reading. At box 116, the micro-controller 62 then clears the pulse count back to zero and a data ready flag is set by the micro-controller at box 118. At box 120, the first byte and the second byte are then individually sent from the micro-controller 62 to the personal computer 64. Once the first byte and the second byte have been sent to the personal computer 64, the micro-controller 62 clears the data ready flag at box 122 and the sequence loops back via line 124 to the increment pulse count.

Figure 9A:
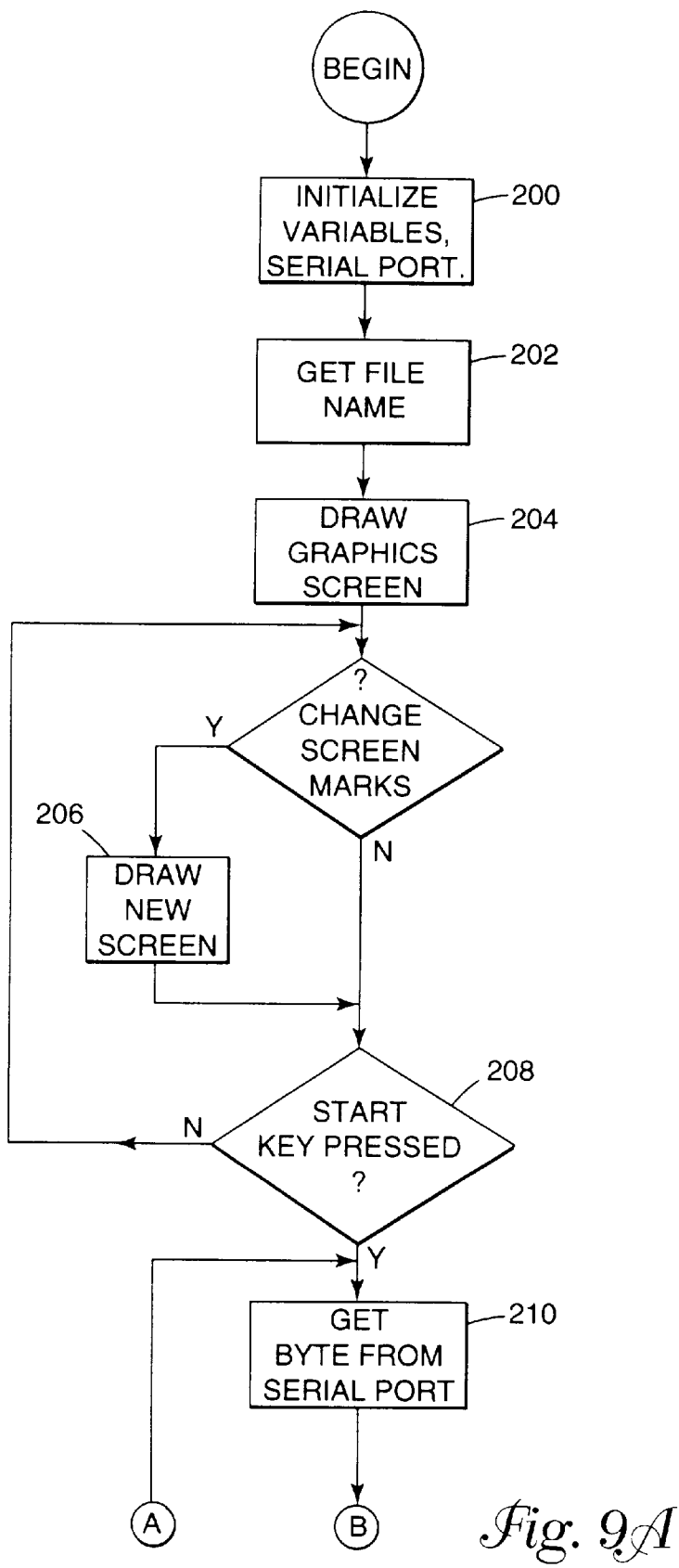
FIGS. 9A–9C show a flow chart illustrating personal computer flow logic suitable for use with the present invention.
Figure 9B:
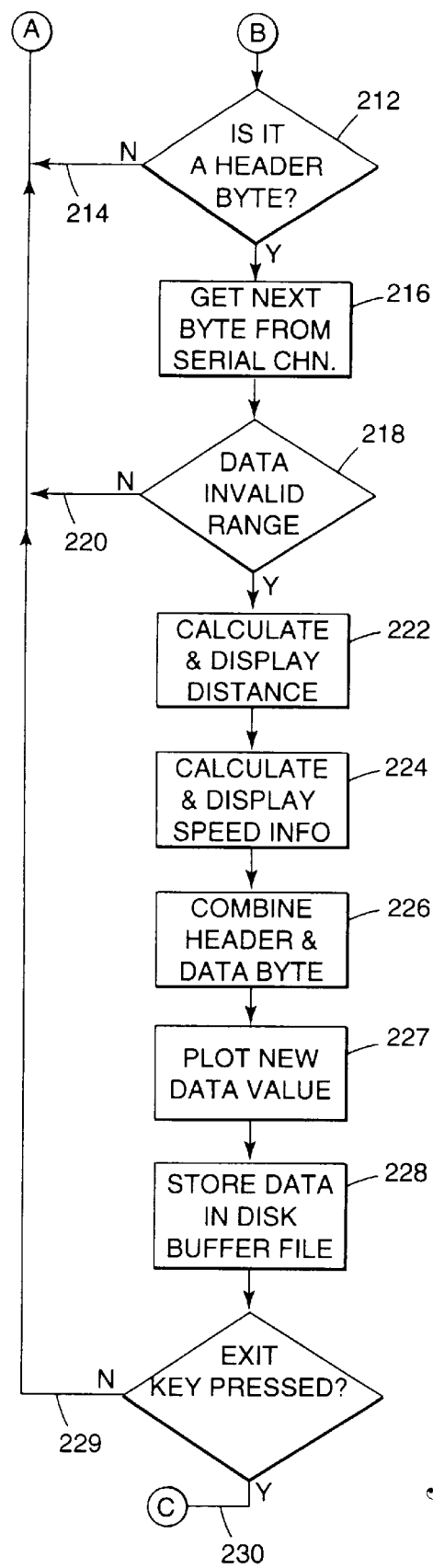
Figure 9C:
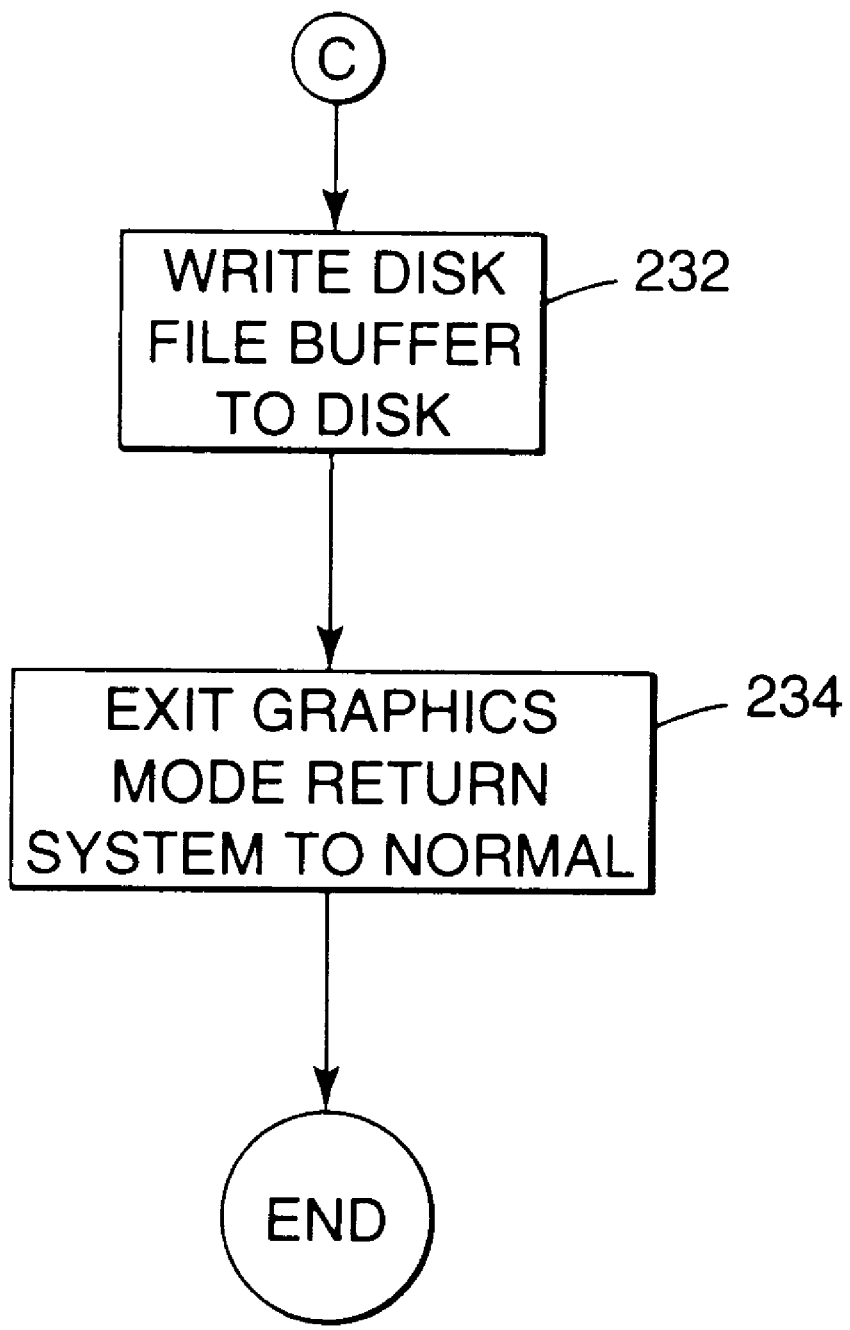

FIGS. 9A–9C show a flow chart illustrating control logic suitable for use in association with the processing unit/personal computer 64 of the detection apparatus 50. As shown in the flow chart at box 200, the personal computer 64 is first powered up and all variables, data arrays, ports, disk buffers and other components are initialized. Next, at box 202, a disk file name is accessed for later storage of data. At box 204, graphics are drawn 204 on the display screen. As shown by box 206, the graphics mode can be switched between a split screen or a full screen mode if desired.

It will be appreciated that the graphics preferably include a graph as shown in FIG. 7. A tendon profile is preferably progressively plotted on the graph in an ongoing manner as the test of a particular tendon is conducted. It will further be appreciated that a graph showing the speed of the cart 52 can also be displayed on the screen.

To access detection data from the micro-controller 62, the start key of the computer keyboard is pressed at box 208. At box 210, the processing unit 64 accesses a first byte from the micro-controller 62 and at box 212 checks whether the byte accessed is a header byte. If the first byte is not a header byte, the sequence loops back via line 214 and the processing unit 64 attempts to access a new first byte. If it is a header byte, the sequence continues and at box 216 a second byte is accessed from the micro-controller 62. The data in the first byte is then analyzed at box 218 to see if the value received is greater than 128. If the value is greater than 128, an error has occurred and the sequence loops back via line 220 such that the processing unit 64 looks for a new first byte. If the value is less than 128, the processing unit 64, at box 222, uses the data to calculate a distance or position value and displays the value on the screen 71. The processing unit 64 also uses the data at box 224 to calculate speed information relating to the speed of the cart 52. If the cart is being moved too fast, such that the processing unit 64 is unable to process all of the data, a warning indicator such as an warning symbol on the screen 71 or an audible alarm is signaled.

Once the calculations are complete, the processing unit 64 combines at box 226 the first and second bytes. Data contained within the bytes that is representative of the reading generated by the ferrous material detector 58 is then plotted at box 227 versus the distance/location data and displayed on the screen 71 such that a tendon profile, as shown in FIG. 7, is progressively generated on the screen 71. At box 228, the coordinates are stored in a disk buffer file. The sequence then loops back via line 229 and the processing unit 64 looks for a subsequent first header byte and the sequence is repeated.

To exit the loop sequence, the exit key on the computer keyboard is pressed at box 230 causing the processing unit 64 to write at box 232 the contents of the disk buffer file to non-volatile memory such as the previously identified file on a disk and exit at box 234 the graphics mode.

FIG. 10 schematically shows an apparatus 350 in accordance with the principles of the present invention that is equipped with an auto-centering feature.

Generally, the apparatus 350 includes a lead sensor or scanning unit 352 preferably comprising a metal detector equipped with a sensor portion or probe, a main sensing unit 354 preferably comprising another metal detector equipped with a sensor portion or probe, a distance meter 356 for measuring a distance traversed by the apparatus 350 in a first direction along a tendon (indicated by arrow 358), and a control system 361 that interfaces with each of the components of the apparatus 350. The control system 362 can include one or more micro-controllers as well as a main data processing unit.

The scanning unit 352 is positioned in front of the main sensing unit 354 and is adapted to continuously scan back and forth along a lateral orientation, indicated by arrows 360, as the apparatus 350 is moved in the direction indicated by arrow 358. Preferably, at least the sensing portion of the scanning unit 352 is reciprocated by means such as a first motor 362 in the lateral orientation indicated by arrows 360. A first lateral position sensor 364 continuously measures or monitors the lateral position of the scanning unit 352. In certain embodiments, at least the sensing portion of the scanning unit 362 is slidably mounted on spaced-apart parallel rods or bars for allowing lateral movement of the unit 362. It will be appreciated that the lateral direction or orientation indicated by arrows 360 is generally transverse with respect to the direction indicated by arrow 358. The scanning unit 352, position sensor 364 and motor 362 together form an exemplary lead sensing arrangement suitable for generating data representative of a lateral position of a tendon as will be described in greater detail below.

The main sensing unit 354 is adapted move in a lateral orientation, indicated by arrows 366, in response to feedback or data provided by the lead sensing arrangement. Preferably, at least a sensing portion of the sensing unit 354 is laterally moved by conventional techniques such as a second motor 368. A second lateral position sensor 370 continuously measures or monitors the lateral position of the sensing unit 354.

In certain embodiments, at least the sensing portion of the main sensing unit 354 is slidably mounted on spaced-apart parallel rods or bars for allowing lateral movement of the unit 354. It will be appreciated that the lateral direction or orientation indicated by arrows 360 is generally transverse with respect to the direction indicated by arrow 358. Also, by way of non-limiting example, the second motor 368 can be a stepper motor or servo-motor having a counter or other conventionally know structure for monitoring the lateral position of the sensing portion of the main sensing unit 354.

In general use, as the apparatus is traversed along a tendon (direction indicated by arrow 358), the scanning unit 352 scans laterally back and forth across the tendon to identify a lateral position of the tendon. Preferably, each lateral sweep has a distance $d_1$ in the range of 6–8 inches. In certain embodiments, the scanning unit 352 completes about one lateral sweep in a time ranging from about ¼ to 2 seconds. Thus, one complete back and forth cycle is preferably completed in about ½ to 4 seconds.

During each sweep across the tendon, the scanning unit 352 preferably takes magnetic readings, and the first lateral position sensor 364 measures or determines the lateral position of the scanning unit 352. The magnetic readings from the scanning unit 352, and the position data from the first lateral position sensor 364, are sent to or sampled by the control system 361. For each sweep, the control system 361 uses the data from the scanning unit 352 and the first lateral position sensor 364 to determine the lateral position $lp_1$ at which a maximum magnetic reading is detected by the scanning unit 354. A maximum reading is typically detected when the probe of the scanning unit 352 is located directly above the tendon. Hence, the lateral position $lp_1$ preferably coincides with a position directly above the tendon.

Figure 10A:
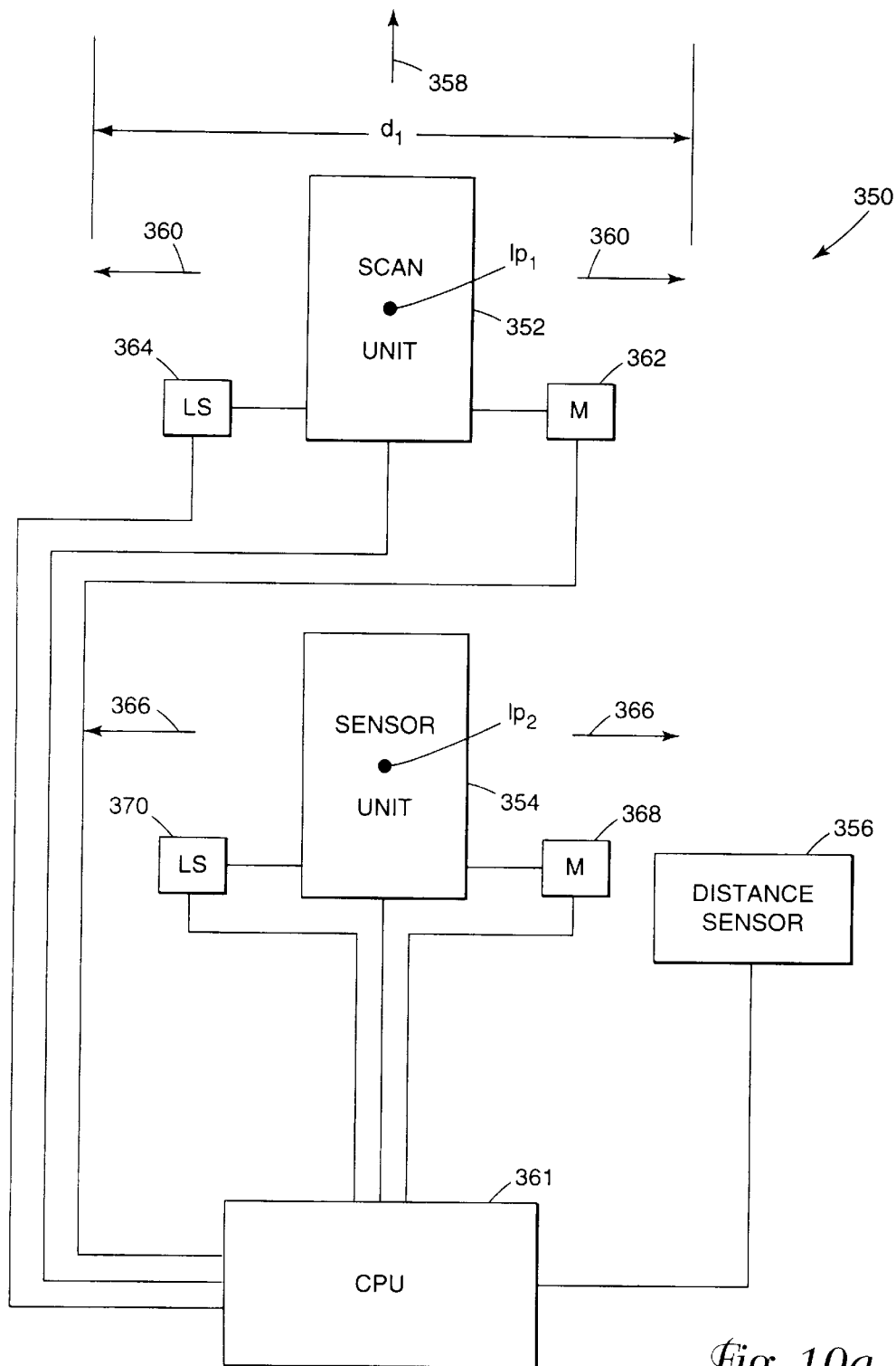
FIGS. 10a and 10b is a schematic diagram illustrating another embodiment or aspect of a sensing apparatus constructed in accordance with the principles of the present invention.
Figure 10B:
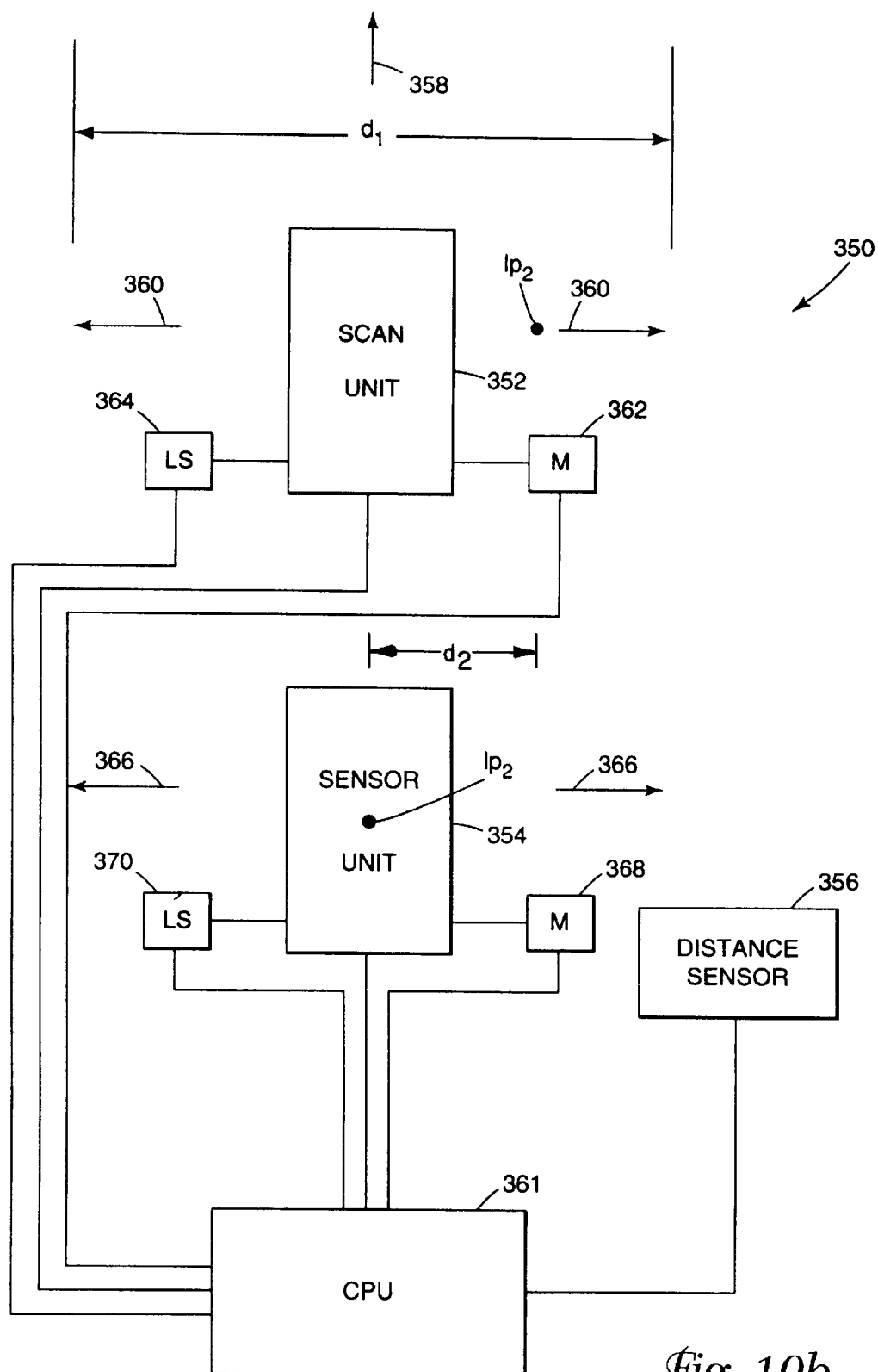

The lateral position $lp_1$ of the maximum reading is then compared by the control system 361 to a lateral position $lp_2$ in which the probe of the sensor unit 354 is oriented. The lateral position $lp_2$ is determined by the control system 361 through the use of lateral position data provided from the second lateral position sensor 370. If the lateral position $lp_2$ of the sensor unit 354 probe is in general alignment with the lateral position $lp_1$ of the maximum reading (as shown in FIG. 10a), no correction is required and the probe of the sensor unit 354 is not moved. By contrast, if the lateral position $lp_2$ varies from the lateral position $lp_1$ by a predetermined distance $d_2$ (as shown in FIG. 10b), such as ¼", the control system 361 causes the second motor 368 to move the sensor unit 354 in the appropriate direction until $lp_2$ aligns with or equals $lp_1$. This action continuously places the sensing unit 354 within a predetermined tolerance, such as ¼ inch, of the tendon desired to be scanned. Preferably, the scanning unit 352 takes one reading every ⅛ inch based upon sampled readings from the first lateral distance sensor 364.

FIGS. 11a–11d show an embodiment of a drive mechanism 400 suitable for oscillating the probe of the lead sensor unit 352. A similar configuration can also be used to move the main sensing unit 352. The mechanism 400 includes a rectangular follower member 402 slidably secured between a pair of rails 404 by rollers 406. The follower member 402 defines an elongated longitudinal slot 408. A pin 410 secured to a disk 412 is inserted within the slot 408. The disk 412 is rotated about a central axis of rotation 414 by the first drive motor 362. For example, torque is transferred from the first motor 362 to the disk 412 by a belt 416 entrained about the disk 412. The probe of the lead sensor unit 352 is preferably secured to a bottom side of the follower member 402.

In use, the first motor 362 causes the disk 412 to rotate via the belt 416. As the disk 412 rotates, the pin 410 functions as a cam and engages the follower member 402 causing the follower member 402 to oscillate along the rails 404 in the lateral direction indicated by arrows 360. As the follower member 402 oscillates, the pin 410 oscillates within the slot 408. The lateral position of the follower member 402 at a given time can be determined by a sensor that monitors the rotational orientation of the disk 412. It will be appreciated that such rotary sensors are conventionally known in the art.

Figure 11A:
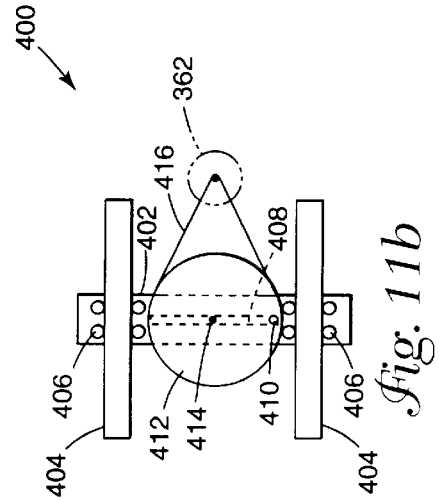
FIGS. 11a–11d schematically illustrate positions of an embodiment of a drive mechanism for oscillating a scanning sensor used in accordance with the principles of the present invention.
Figure 11B:
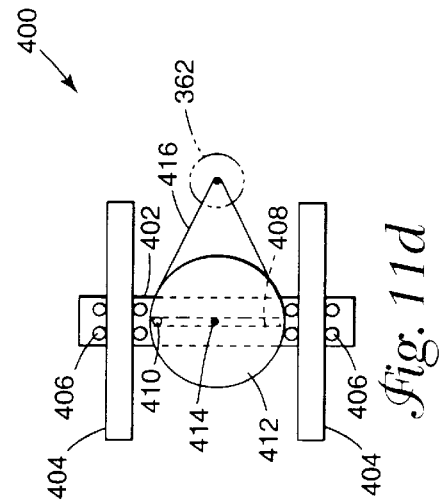
Figure 11C:
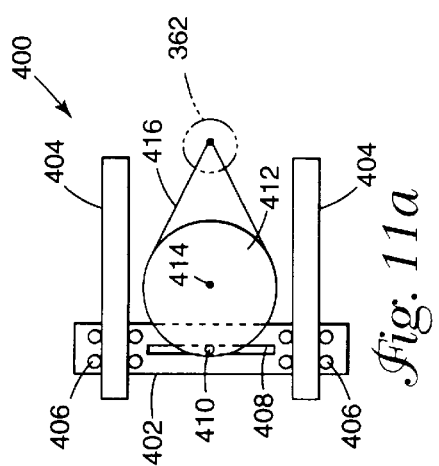
Figure 11D:
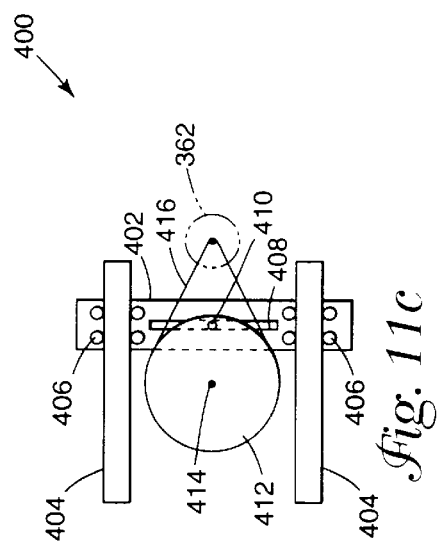

The follower member 402 completes one oscillation cycle per rotation of the disk 412. FIGS. 11a–d show four separate positions of the follower member 402 during a single oscillation cycle. For example, FIG. 11a shows the follower member 402 at a left-most position, FIG. 11b shows the follower member 402 in a central position, FIG. 11c shows the follower member 402 in a right-most position, and FIG. 11d shows follower member 402 back at the central position.

With regard to the foregoing description, it is to be understood that changes may be made in detail, especially in matters of the construction materials employed and the shape, size, and arrangement of the parts without departing from the scope of the present invention. For example, in certain embodiments, a single lead sensor probe elongated in a lateral direction, or multiple lead sensor probes spread out in a lateral direction, can be used to provide data suitable for centering the main sensor unit above a tendon. Also, in certain embodiments, a lead sensor assembly can be used to provide information to an operator instructing the operator to manually turn a test apparatus in a particular direction in order to keep a main sensor unit centered over a tendon. For example, left and right turn arrows can be displayed on a computer screen to advise an operator which way the test apparatus should be steered to maintain alignment over the tendon. It is intended that the specification and depicted embodiment be considered exemplary only, with a true scope and spirit of the invention being indicated by the broad meaning of the following claims.

What is claimed is as follows:

1. A nondestructive detection apparatus for detecting failures within a length of tendon in a reinforced concrete slab, the detection apparatus comprising:

a vehicle adapted to be moved along the concrete slab;

a main sensing mechanism connected to the vehicle for taking readings of the tendon as the vehicle is moved along the concrete slab;

a distance instrument connected to the vehicle for measuring a distance traversed by the vehicle as the vehicle is moved along the concrete slab;

a controller that interfaces with the main sensing mechanism and the distance instrument, the controller being constructed and arranged to sample the readings as the vehicle is moved along the slab; and a lead sensing arrangement positioned ahead of the main sensing mechanism for generating data representative of a lateral position of the tendon.

2. The detection apparatus of claim 1, wherein the controller converts the readings from analog to digital readings.

3. The detection apparatus of claim 2, further comprising a processing unit that interfaces with the controller, wherein the processing unit receives the digital readings from the controller, calculates corresponding distance data, and generates a graph in which the digital readings are plotted verses the corresponding distance data to produce a profile for the length of tendon.

4. The detection apparatus of claim 3, further comprising a screen that interfaces with the processing unit for displaying the graph.

5. The detection apparatus of claim 3, further comprising memory for storing the digital magnetic readings and the distance data.

6. The detection apparatus of claim 1, wherein the distance instrument comprises a rotary encoder cooperating with a wheel of the vehicle.

7. The detection apparatus of claim 1, wherein the main sensing mechanism comprises a metal detector.

8. The detection apparatus of claim 7, wherein the metal detector includes a probe adapted to be positioned proximate to the concrete slab.

9. The detection apparatus of claim 8, wherein the probe is mounted on a slide plate that is pivotally connected to the vehicle by a pivot member and is adapted to slide across the concrete slab.

10. The detection apparatus of claim 1, further comprising means for automatically centering the main sensing mechanism over the tendon.

11. A method for nondestructively detecting tendon failures in a reinforced concrete slab comprising:

locating a length of tendon within the concrete slab;

moving a metal detector longitudinally along the length of tendon;

generating sets of data as the metal detector is moved longitudinally along the length of tendon, each set of data including:

a first value representative of the proximity of the tendon to the metal detector at the time the first reading was generated; and a second value representative of a position along the length of tendon at which the first reading was generated.

12. The detection apparatus of claim 1, further comprising a drive arrangement for laterally oscillating the lead sensing mechanism relative to the tendon.

13. The detection apparatus of claim 1, further comprising a drive motor for moving the main sensing unit laterally in response to the data generated by the lead sensing arrangement.

14. A nondestructive detection apparatus for detecting failures within a length of tendon in a reinforced concrete slab, the detection apparatus comprising:

a vehicle adapted to be moved along the concrete slab;

a main sensing mechanism for taking readings of the tendon as the vehicle is moved along the concrete slab;

a distance sensor for measuring a longitudinal distance traversed by the vehicle as the vehicle is moved along the concrete slab;

a lead sensing arrangement positioned ahead of a sensing portion of the main sensing mechanism for generating lateral position data representative of a lateral position of the tendon;

a drive mechanism adapted for moving at least the sensing portion of the main sensing unit mechanism laterally relative to the tendon; and a controller that interfaces with the main sensing mechanism, the distance instrument and the lead sensing arrangement, the controller being adapted to sample the readings generated by the main sensing mechanism, the controller also being adapted to cause the drive mechanism to move at least the sensing portion of the main sensing unit laterally in response to the lateral position data generated by the lead sensing arrangement.

15. The apparatus of claim 14, wherein the lead sensing arrangement includes a sensing portion that is adapted to be laterally oscillated relative to the tendon.

16. The apparatus of claim 14, wherein the lead sensing arrangement includes a lateral position sensor for monitoring the lateral position of a sensing portion of the lead sensor arrangement.

17. A nondestructive detection apparatus for detecting failures within a length of tendon in a reinforced concrete slab, the detection apparatus comprising:

a vehicle adapted to be moved along the concrete slab;

a main sensing mechanism for taking readings of the tendon as the vehicle is moved along the concrete slab;

a distance sensor for measuring a longitudinal distance traversed by the vehicle as the vehicle is moved along the concrete slab;

a lead sensing arrangement positioned ahead of a sensing portion of the main sensing mechanism for generating lateral position data representative of a lateral position of the tendon; and a controller that interfaces with the main sensing mechanism, the distance instrument and the lead sensing arrangement, the controller being adapted to sample the readings generated by the main sensing mechanism, the controller also being adapted to use the lateral position data generated by the lead sensing arrangement to determine whether the sensing portion of the main sensor is positioned over the tendon.

18. A nondestructive detection apparatus for detecting failures within a length of tendon in a reinforced concrete slab, the detection apparatus comprising:

a vehicle adapted to be moved along the concrete slab;

a main sensing mechanism for taking readings of the tendon as the vehicle is moved along the concrete slab;

a distance sensor for measuring a longitudinal distance traversed by the vehicle as the vehicle is moved along the concrete slab;

a controller for sampling the readings generated by the main sensing mechanism; and means for auto-centering the sensing portion of the main sensing mechanism over the tendon.

19. A method for nondestructively detecting tendon failures in a reinforced concrete slab comprising the steps of:

locating a length of tendon within the concrete slab;

moving metal sensing means and mapping means longitudinally along the length of tendon to create first and second signals, the first signal being generated by the metal sensing means and the second signal being generated by the mapping means; and plotting a first parameter verses a second parameter, the first parameter being based on the first signal and representative of the proximity of the tendon to the metal sensing means, and the second parameter being based on the second signal and representative of a distance traversed along the tendon, wherein a profile for the length of tendon is generated by plotting the first and second parameters.

20. The method of claim 19, further comprising the step of sampling the first signals at predetermined distance intervals along the length of tendon.

21. The method of claim 20, wherein the first signal is sampled at least one time per inch traversed along the length of tendon.

22. A nondestructive detection apparatus for detecting failures within a length of tendon in a reinforced concrete slab, the detection apparatus comprising:

a vehicle adapted to be moved along the concrete slab;

a main sensing mechanism connected to the vehicle for taking readings of the tendon as the vehicle is moved along the concrete slab;

a distance instrument connected to the vehicle for measuring a distance traversed by the vehicle as the vehicle is moved along the concrete slab;

a controller that interfaces with the main sensing mechanism and the distance instrument, the controller being constructed and arranged to sample the readings at least one time per inch traversed by the vehicle; and a lead sensing arrangement positioned ahead of the main sensing mechanism for generating data representative of a lateral position of the tendon.

23. The method of claim 11, further comprising plotting the data sets on a graph having a first axis for the first values and a second axis for the second values, wherein the plot provides a visual profile of the length of tendon.

24. The method of claim 11, further comprising the step of generating the first values at predetermined distance intervals along the length of tendon.

25. The method of claim 20, wherein the first values are sampled at least one time per inch traversed along the length of tendon.

26. The method of claim 23, wherein discontinuities in the profile are representative of breaks in the tendon.

* * * * *